United States Patent
Bianchi et al.

(10) Patent No.: US 7,468,387 B2
(45) Date of Patent: Dec. 23, 2008

(54) CRYSTALLINE FORMS OF IMIDOALKANPERCARBOXYLIC ACIDS

(75) Inventors: Ugo Piero Bianchi, Verona (IT); Roberto Garaffa, Milan (IT)

(73) Assignee: Solvay Solexis S.p.A., Milan (IT)

( * ) Notice: Subject to any disclaimer, the term of this patent is extended or adjusted under 35 U.S.C. 154(b) by 227 days.

(21) Appl. No.: 10/519,835

(22) PCT Filed: Jul. 8, 2003

(86) PCT No.: PCT/EP03/07303

§ 371 (c)(1), (2), (4) Date: Jul. 13, 2005

(87) PCT Pub. No.: WO2004/007452

PCT Pub. Date: Jan. 22, 2004

(65) Prior Publication Data

US 2005/0245590 A1 Nov. 3, 2005

(30) Foreign Application Priority Data

Jul. 12, 2002 (IT) .......................... MI2002A1537

(51) Int. Cl.
*A61K 31/4035* (2006.01)
*C07D 209/44* (2006.01)

(52) U.S. Cl. ....................... 514/417; 548/470; 548/472; 548/473; 514/416

(58) Field of Classification Search ................. 548/470, 548/472, 473, 950, 952; 514/210.01, 210.02, 514/416, 417
See application file for complete search history.

(56) References Cited

U.S. PATENT DOCUMENTS

| 5,520,844 A | * | 5/1996 | Venturello et al. | ..... 252/186.42 |
| 5,536,434 A | * | 7/1996 | Venturello et al. | ........... 510/375 |
| 5,688,434 A | * | 11/1997 | Venturello et al. | ..... 252/186.42 |

FOREIGN PATENT DOCUMENTS

| EP | 0325289 A1 * | 1/1989 |
| EP | 0 325 288 | 7/1989 |
| EP | 0 325 289 | 7/1989 |
| EP | 0 349 940 | 1/1990 |
| EP | 0 490 409 | 6/1992 |
| EP | 0 556 769 | 8/1993 |
| EP | 0 560 155 | 9/1993 |
| EP | 0 780 374 | 6/1997 |
| EP | 0 852 259 | 7/1998 |
| EP | 0 895 777 | 2/1999 |
| EP | 1 074 607 | 2/2001 |
| WO | 00 27960 | 5/2000 |
| WO | 00 27969 | 5/2000 |
| WO | 00 27982 | 5/2000 |

OTHER PUBLICATIONS

Suzuki et al (1993): STN International HCAPLUS database, Columbus (OH), accession No. 1993: 562932.*
Feeder, N. et al. "Four omega-Phthalimidoaliphatic Peracids", Acta Cryst., vol. C52, No. 6, pp. 1516-1520, XP009018676 1996.

* cited by examiner

*Primary Examiner*—Golam M Shameem
(74) *Attorney, Agent, or Firm*—Oblon, Spivak, McClelland, Maier & Neustadt, P.C.

(57) ABSTRACT

Imidoalkancarboxylic acids of formula (I) are described, wherein A, X and M are as defined in the application, said acids being in a crystalline form which in contact with water gives rise to crystals having sizes lower than 30 micron.

16 Claims, No Drawings

CRYSTALLINE FORMS OF IMIDOALKANPERCARBOXYLIC ACIDS

The present invention relates to imido-alkan percarboxylic acids, having an improved bleaching efficacy, usable also at a moderate temperature, even of the order from 10° C. to 30° C. for the industrial and commercial applications in the detergency and disinfection.

More specifically the invention relates to a new crystalline form of imido-alkanpercarboxylic acids, stable at the solid state but when suspended in water, it is spontaneously transformed into crystals of various crystalline form, stable in aqueous medium and having an average particle size lower than 30 micron, preferably lower than 8 micron, in particular lower than or equal to 2 micron. The imido-alkanpercarboxylic acids obtained with said sizes have a higher bleaching efficacy, the concentration being equal, with respect to those having sizes higher than 30 micron and furthermore they can be formulated in dispersions, for example aqueous, for industrial and commercial applications by using reduced amounts of chemical additive agents, in particular suspending agents, with respect to those requested by the prior art.

It is known that imido-alkanpercarboxylic acids can be obtained for example as slurries. They are known and used as bleaching agents in detergent formulations, or as main components of disinfectant or oxidizing compositions. The compositions containing said acids combine good belaching properties with a good stability to storage.

The processes for the preparation of imido-alkanpercarboxylic acids are well known in the literature and comprise the oxidation, in the presence of a mixture of hydrogen peroxide and of a strong acid, of the imido-alkancarboxylic acid precursors. The precursor, in the case of the phthalimidoalkanpercarboxylic acids, is obtained by condensation of phthalic anhydride, or phthalic acid with aminoacids or lactams, by reaction, optionally in the presence of water, at a pressure from 1 to 30 bar and at temperatures ranging from 100° C. to 250° C., with reaction times from 1 to 20 hours. See for the example EP 325,289, EP 325,288, EP 349,940. EP 490,409 describes a process to obtain with high yields percarboxylic acids wherein one operates in the presence of particular organic solvents for example $CH_2Cl_2$ and $CHCl_3$, by separating at the end of the reaction the organic solvent containing the percarboxylic acid from the aqueous phase containing sulphuric acid and hydrogen peroxide. The useful product is then recovered by removal of the organic solvent. In EP 560,155 various processes of the organic solution treatment with water are described, by which for example ε-phthalimido-peroxyhexanoic acid (PAP) as wet crystalline cake is finally obtained, by filtration or centrifugation of aqueous slurries containing organic solvents, for example $CH_2Cl_2$ or ethyl acetate, with residual water contents of the order of 20% by weight and traces of residual solvent in the range 50-2,500 ppm.

Generally the residual amounts of chlorinated solvents accepted in the alkanpercarboxylic acid formulations are very low. To lower the residual content of said chlorinated solvents in the obtained cake, as said, a subsequent purification treatment with a non chlorinated solvent for example ethylacetate must be carried out, as described in EP 556,769. However the obtained alkanpercarboxylic acid contains not negligible amounts of the solvent used in the last purification.

Furthermore, at the end of said treatments to lower the chlorinated solvent content by using the processes of the above patents, the water percentage by weight in the alkanpercarboxylic acid is of the order of 20% or higher. This water amount is too high for the prepartion of alkanpercarboxylic acid solid formulations and it is generally reduced by drying processes, which must be slow to avoid explosive peracid decompositions. This is a critical phase of the industrial processes for obtaining peracids, due to its dangerousness and due to its poor productivity. Besides with said drying processes a constant value of the residual water content should be obtained, as required to carry out the following working processes of the solid peracid.

EP 780,374 describes a process to reduce the water content of imido-alkanpercarboxylic acids, initially higher than 12% by weight, to a constant value and lower than 10% by weight, said process comprising the heating steps of a suspension of an imido-alkanpercarboxylic acid in water until the complete solid melting, subsequent separation of the organic phase from the aqueous phase and recovery of the organic phase containing the imido-alkanpercarboxylic acid. The process of said patent is based on the fact that the pure imido-alkanpercarboxylic acids, for example obtained by crystallization from organic solutions, have a melting point very close to the decomposition temperature; while the imido-alkanpercarboxylic acids in the presence of water are such to melt at a temperature significantly lower than the melting temperature, by forming eutectics. The water content constancy in the final peracid, typical of the eutectic composition, is a very important factor for the subsequent product finishing treatments. The physical form of the peracid obtained with said process has the advantage to allow to avoid the product granulation, which is carried out when the peracid is in the powder form to make easier the subsequent operations during the formulation and/or transport.

It is known in the prior art that it is preferred the use in the bleach of crystalline peroxycarboxylic acids, obtainable as such in solid phase and having a high title, and usable even in absence of hydrogen peroxide. Among them, sparingly water soluble peroxycarboxylic acids are preferred, because they are more suitable for the development of not very aggressive compositions for users, but effective in these applications already at room temperature. Among these sparingly water soluble crystalline peroxycarboxylic acids, imido-alkanpercarboxylic acids are in particular known, for example ε-phthalimido-peroxyhexanoic acid ("PAP") sold by Solvay Solexis (former Ausimont) by the trademark Eureco®. Said peracids are known from EP 325,288 and EP 325,289 in the name of the Applicant, as preferred for the production on an industrial scale and for the applications on commercial scale in the mentioned fields. For the detergency use see in particular the compositions of said peracids described in EP 852,259 in the name of the Applicant. For the uses in the fields of the body care, of the cosmetics and pharmaceutics, see the compositions described in EP 895,777, EP 1,074,607 in the name of the Applicant.

The ε-phthalimido-peroxyhexanoic acid ("PAP") is particularly preferred in the above application fields for its exceptional stability in crystalline solid phase and for the consequent safety with which it can be handled and used on a large scale. The exceptional thermal stability of the PAP in crystalline form, also at the solid state of technical degree, obtained both by experimental laboratory processes and by industrial processes, is known in the prior art and distinguishes it from most of the known crystalline peroxycarboxylic acids, see for example EP 490,409 in the name of the Applicant. This higher PAP chemico-physical stability is lower when the PAP is present under the solute form in a solution of a chemically compatible and inert solvent, for example water, within the solubility limits set by the solution temperature. A contribution to the exceptional PAP stability at the solid state seems therefore to derive from the nature itself of its crystalline form known in the prior art, since easily obtainable by PAP crystallization from its solutions in organic solvents, for example as described in the already mentioned patents EP 556,769 and EP 560,155, or also by PAP solidification from one of its melted phase of eutectic composition, in the presence of water, see EP 780,374. In all said cases the obtained PAP crystals have on an average sizes higher than 100 micron. The imido-alkanpecarboxylic acids in the known crystalline form are not obtainable by crystallization from an aqueous solution, owing to their low solubility in water. An useful implication for the practical purposes of this property of imido-alkanpercarboxylic acids is the substantial stability in the time of the aqueous crystal dispersions of said peracids, which do not show phenomena of morphological modification by spontaneous recrystallization. Therefore said aqueous dispersions maintain their chemico-physical characteristics even for long storage times.

It is also known that the performances of the formulations based on sparingly water soluble crystalline imido-alkanpercarboxylic acids, especially in the applications at low temperature, are more effective and suitable if the peracid in crystalline phase is present under the form of particles having sizes on an average lower than 100 micron. In this case indeed in the application phase the bleach action takes place without undesired phenomena, as the presence of solid residues on treated tissues or a local colour fading or a located damage of the less resistant fibers. See for example patent application WO 00/27,960. Said particles having on an average sizes lower than 100 micron can be obtained by two milling operations in series starting from crystals obtained by the processes of the prior art. It is known indeed that to have a more effective milling to obtain particles having on an average sizes lower than 100 micron, subsequent millings must be applied utilizing techniques having a complementary effect. See patent application WO 00/27,969. With said particular milling technologies it is possible to obtain formulations of imido-alkanpercarboxylic acids wherein the peroxyacid is present in a stable form under the form of particles having sizes on an average lower than 100 micron. Tests carried out by the Applicant have shown that said sizes can be reduced to sizes on an average of 35 micron. See the comparative Examples. The drawback of said milling technologies is that mills for milling are required involving significant investment and working, maintenance and process and quality control costs. Furthermore said technologies imply additional costs for the use of specific chemical additives to make milling easier, and for the maintenance in the time of the so obtained microscopic particles of the imido-alkanpercarboxylic acids. Indeed in absence of said additives the particles would tend to aggregate again. The use of said specific additives makes easier the hard milling of said peracids reducing the mechanical stress to which said crystalline peracids are subjected. In practice said additives allow to obtain particles of said peracids having on an average sizes lower than 100 micron, even to 35 micron and in a stable physical form in the time.

It is known, furthermore, see patent application WO 00/27,982, that the purity of imido-alkanpercarboxylic acids in the compositions must be high and the residual impurities in said peracids must be lower than 5% by weight. Furthermore pollutants must be absent since could accidentally enter the composition during the composition and milling processes and which negatively influence the duration in the time and the intrinsic safety of said compositions, in particular of those having a high content of imido-alkanpercarboxylic acids. When milling is used, the use of a peracid originally having a high purity and of accurate working techniques allow in the industrial practice to obtain peracid particles having on an average sizes of the order of 35 micron and chemically stable in the time.

It is also known that in the case of compositions of imido-alkanpercarboxylic acids finely dispersed in aqueous phase, the selection of effective suspending agents, capable to assure in the time the desired chemico-physical stability of the system and the constancy of its Theological properties, is critical. To obtain these properties the concentration of said suspending agents is not reducible beyond certain values, and their cost results not negligible compared with that total of the composition. See for example EP 1,074,607.

The need was felt to have available imido-alkanpercarboxylic acids in a physical form such to assure an improved bleaching efficacy and in disinfection allowing the use of said peracids also at temperatures of 10° C.-30° C. in detergency and in disinfection, without making use of the milling technologies and the additives required for milling as described in the prior art, said imido-alkanpercarboxylic acids being capable to give compositions wherein the used amount of suspending agents was lower than that of the compositions of the prior art, even maintaining the same chemico-physical stability and the constancy of the rheological properties in the time.

The Applicant has unexpectedly and surprisingly found imido-alkanpercarboxylic acids allowing to solve the above technical problem.

An object of the present invention are imido-alkanpercarboxylic acids having formula (I):

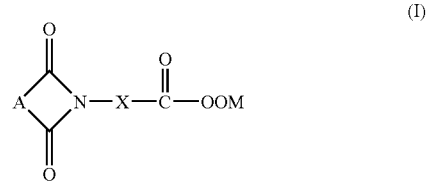

wherein A indicates a group selected from the following:

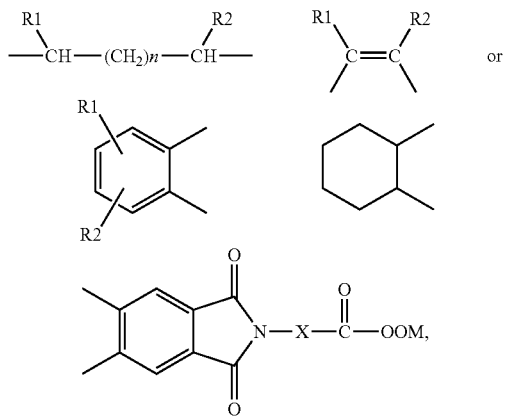

wherein:

n is an integer 0, 1 or 2,

R1 has one of the following meanings: hydrogen, chlorine, bromine, $C_1$-$C_{20}$ alkyl, $C_2$-$C_{20}$ alkenyl, aryl or alkylaryl, R2 is hydrogen, chlorine, bromine or a group selected from the following: —$SO_3M$, —$CO_2M$, —$CO_3M$ or —$OSO_3M$, M has the meaning of hydrogen, an ammonium alkaline metal, or an equivalent of an alkaline-earth metal, X indicates a $C_1$-$C_{19}$ alkylene or arylene;

said imido-alkanpercarboxylic acids being in a crystalline form, herein called alpha, stable at storage at the solid state, and when dispersed in water it is transformed into crystals of the known crystalline form of the prior art (herein called beta), stable in aqueous environment, said novel crystals of beta crystalline form having average sizes lower than 30 micron, preferably lower than 10 micron, more preferably lower than 8 micron, particularly lower than or equal to 2 micron; the alpha crystalline form being characterized with respect to the known beta crystalline form of the prior art in that the respective spectra obtained by the X Ray Diffraction and the Surface Infrared Spectroscopy (IR/S) techniques show, with respect to those of the beta form of the same peracid, a different spectral imagine at X rays and a typical absorption shift in the 1697-1707 $cm^{-1}$ zone at IR/S towards higher frequencies, of the order of about 8-10 $cm^{-1}$.

The crystals of the alpha form have the same solubility in water of the crystals of the prior art (beta form). Therefore they form aqueous dispersions.

In particular in the case of the ε-phthalimido-peroxyhexanoic acid (PAP) the beta form known in the prior art shows:
at X rays: typical peaks at 18.0 and 18.7 and no quadruplet at 24.2-25.0 [°2θ],
at the IR/S spectrum: typical peak with maximum absorption in the 1699-1704 $cm^{-1}$ zone, for dried crystals having water absorption at 3450-3500 $cm^{-1}$ lower than 5%;

while, for the same PAP compound the alpha form shows the following spectral characteristics:
at X rays: typical peaks at 17.5 and 19.0 and typical quadruplet at 24.2-25.0 [°2θ],
at IR/S spectrum: typical peak with maximum absorption in the 1707-1712 $cm^{-1}$ zone for dried crystals, having a water absorption at 3450-3500 $cm^{-1}$ lower than 5%.

The X ray spectrum is carried out on dried powder samples for 48 h at 20° C. under vacuum (residual pressure 10 mmHg).

Said alpha crystalline form is therefore distinguishable from the known beta crystalline form of the prior art of the same imido-alkanpercarboxylic acids both by the above characterization methods, and mainly due to the fact that suspended in water it is spontaneously transformed into stable crystals of different form (beta), stable in water and having sizes on an average lower than 30 micron, preferably lower than 10 micron, more preferably lower than 8 micron and in particular of the order of 2 micron.

The crystal sizes of alpha form are not critical for the obtaining of crystals of the beta form having the above mentioned sizes.

The imido-alkanpercarboxylic acids in alpha crystalline form can be formulated in solid compositions, for example granulated with the techniques used in the prior art for crystals of beta type for their use in the detergency and disinfection field. See for example EP 852,259, herein incorporated by reference.

A further object of the present invention are imido-alkanpercarboxylic acids of beta crystalline form, obtainable by dispersing in water crystalline particles of the corresponding alpha form, said particles of beta crystalline form having average sizes lower than 30 micron, preferably lower than 10 micron, more preferably lower than 8 micron, in particular lower than or equal to 2 micron.

A further object of the present invention are compositions of imido-alkanpercarboxylic acids, in particular in aqueous phase compositions, containing said peracids under the form of beta crystalline particles having sizes, on an average, lower than 30 micron, preferably lower than 10 micron, more preferably lower than 8 micron, in particular lower than or equal to 2 micron, obtained by treating the corresponding alpha form of the peracid, as mentioned above.

The peracid concentration in the beta form, having sizes lower than those of the prior art, in said compositions ranges from 0.5% to 25%, expressed in per cent by weight based on the total of the composition.

As said, the beta form crystals are stable both in aqueous dispersion and at the solid state. It has been surprisingly and unexpectedly found by the Applicant that the crystals in beta form, having the above sizes, can be formulated even in aqueous phase using very reduced amounts of suspending agents, even less than ⅕ by weight with respect to those used to prepare the commercial compositions having an aqueous base containing imido-alkanpercarboxylic acids obtained by the milling techniques of the prior art.

In particular it is possible to use suspending additives, for example polymers as xanthan rubber, at concentrations, expressed in percentages by weight from 0.05% to 0.1% based on the total of the composition, instead of the usual concentrations of 0.40-0.60% by weight.

The amount of suspending additives which can be used in said compositions, expressed in percentages by weight on the total of the composition is from 0.05% to 0.6%, preferably from 0.05% to 0.1%.

Besides, to the invention compositions the other conventional additives, for example surfactants, preferably selected from those nonionic and/or anionic, in the usual concentrations useful for the final product performances, can be added.

Optionally it is possible to add to said compositions hydrogen peroxide at concentrations, expressed in percentages by weight, from 0 to 10% based on the total of the composition.

The compositions obtained from said imido-alkanpercarboxylic acids, in the crystalline sizes of beta form on an average lower than 30 micron, result stable in the time from the chemical and physical point of view.

Said compositions are advantageously usable in the bleach and disinfection field with lower costs and performaces higher than those obtainable with the known compositions of the prior art, in particular for the applications at room temperature and at low temperatures. As said, the amount of suspending additives in said compositions is lower than that used in the compositions of the known imido-alkanpercarboxylic acids of the prior art.

The beta crystalline imido-alkanpercarboxylic acids of the present invention having the average particle sizes in the above limits, are obtainable by an advantageous process, feasible on a large scale, safe and not very expensive, wherein milling additives are not used, thus avoiding potential pollutions of the imido-alkanpercarboxylic acids.

In said process particles of the imido-alkanpercarboxylic acid in alpha form, stable at the solid state but unstable in aqueous dispersion, are first obtained, then transformed, as described, into the stable beta form.

To obtain the imido-alkanperoxycarboxylic acids of formula (I) in the beta crystalline form, having the above sizes, the peracid particles in the alpha form are suspended in a stirred aqueous phase and maintained at temperatures from 0° C. to 70° C., preferably from 20° C. to 65° C., more preferably from 40° C. to 60° C., for a time ranging from 1 minute to 90 minutes, preferably from 10 minutes to 60 minutes, more preferably from 20 minutes to 45 minutes.

A further object of the present invention is a process for the preparation of imido-alkanperoxycarboxylic acids of formula (I) having particles in the alpha crystalline form, said process comprising the following steps:

I) peroxidation in the presence of hydrogen peroxide and of a strong acid generally at temperatures comprised between 5° C. and 50° C., of an imido-alkancarboxylic acid precursor obtainable by reaction of:
a) an anhydride of formula:

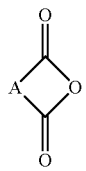

or its corresponding acids, A being as above, with
b1) an aminoacid of formula:

X being as above, or
b2) a lactam of general formula:

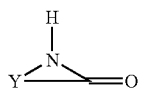

Y having the meanings of X, preferably a $C_3$-$C_{19}$ alkylene;
c) water;
at temperatures in the range 100° C.-250° C., under pressure of an inert gas from 1 to 30 bar (0.1-3 MPa), for reaction times from 1 to 20 hours;
II) obtaining of a melted phase of eutectic composition of the imido-alkanperoxycarboxylic acids of formula (I) by heating a suspension in water of said peracids until the complete solid melting, said eutectic having a composition on a molar basis of no more than two moles of water/peracid mole;
III) separation from the melted organic phase of eutectic composition from the balanced aqueous phase, and recovery of the melted organic phase containing the imido-alkanpercarboxylic acid;
IV) quench of the melted organic phase and obtaining of the phase called herein alfa, stable at the solid state (but unstable at contact with water), as above.

Said quench of step IV) of the process can be carried out in various ways. For example by dripping the melted organic phase of eutectic composition in liquid nitrogen. Another quench method is for example the dripping in cold water, under stirring, having a temperature for example lower than 15° C. To obtain only the alpha form, the skilled man of the field is easily able to determine the most suitable temperature, keeping in mind that as the temperature increases, the beta form can be contemporaneously obtained together with the alpha form. Another quench method is the percolation of the melted phase on one, for example metal, surface or on two, for example metal, surfaces coupled and cooled at temperatures lower than 30° C.

In step I) the ratio by moles generally between a/(b1 or b2)/c is in the range 1/0.8:1.2/0.5:3. Preferably the ratio by moles a/(b1 or b2)/c is comprised between 1/1.01:1.1/0.5:2.5, more preferably between 1/1.05:1.1/1-2.

In step I) it is preferred to react the anhydride a), or the corresponding acid, with the lactam b2).

Among the compounds of class a1) the following anhydrides or the corresponding acids can be mentioned: succinic, glutaric, maleic, trimellitic, phthalic, pyromellitic and alkyl- or alkenyl-succinic anhydride. Preferably the phthalic anhydride or the phthalic acid are used.

Among the class b1) compounds the following can be mentioned: omega-aminobutyric, omega-aminovalerianic, omega-aminocaproic and omega-aminolauric acids.

Among the compounds of class b2) it can be mentioned as preferred: gamma-pyrrolidone, delta-piperidone, epsilon-caprolactam and omega-laurolactam, epsilon-caprolactam (CPL) is particularly preferred.

Preferably in step I) the temperature is in the range 130° C.-180° C. and the pressure between 4 and 8 bar.

At the end of step I) a solvent, preferably $CH_2Cl_2$ and $CHCl_3$, more preferably $CH_2Cl_2$, is preferably added to make easier the subsequent peroxidation of the product.

The last solvents indeed, as described in the patent application EP 780,373 in the name of the Applicant, are the most suitable to carry out the successive peroxidation operation.

Among imido-alkanpercarboxylic acids it can be mentioned the phthalimido-peracetic acid, ε-phthalimido peroxyhexanoic acid, 3-phthalimido-perpropionic acid, 4-phthalimido-perbutyric acid, 2-phthalimido-diperglutaric acid, 2-phthalimido-dipersuccinic acid, 3-phthalimido-perbutyric acid, 2-phthalimido-perpropionic acid, 3-phthalimido-diperadipic acid, naphthalimido-peracetic acid, 2-phthalimido-monopersuccinic acid.

In step II) to reduce the amount of water, sequestrants can be added in the aqueous phase. For example there can be mentioned hydroxycarboxylic acids, as citric acid; amino-policarboxylic acids, as ethylendiaminotetramethylphosphonic acid (EDTMP); pyridincarboxylic acids, such as dipicolinic acid; polyphosphonic acids, for example 1-hydroxy-ethyliden-1,1-diphosphonic acid (HEDP).

Crystalline imido-alkanperoxycarboxylic acids of alpha form obtained by the above process, are stable at the solid state, as said and they clearly distinguish themselves from the same crystalline acids in beta form since they are spontaneously transformed into the corresponding microcrystals of beta form by mere contact with an aqueous phase.

As said, the so obtained crystals of imido-alkanperoxycarboxylic acids of beta form distinguish themselves from those obtained by the known methods of the prior art (milling) by the improved bleaching properties and the lower amount of chemical additives necessary for the preparation of the corresponding compositions. The imido-alkanperoxycarboxylic acid crystals of beta form of the invention have on an average sizes clearly lower than those obtainable by the known milling methods of the prior art.

Said microcrystals in beta form obtained by the invention process from crystalline imido-alkanperoxycarboxylic acids in alpha form, besides the specific bleach activity, are more effective than the crystals obtained according to the methods of the prior art also in terms of antibacterial and disinfectant activity, especially in the applications at room temperature (15° C.-25° C.) or at lower temperatures.

As said, the microcrystals of the imido-alkanperoxycarboxylic acids in beta form of the invention are of particular interest since they require lower amounts of chemical additives for obtaining compositions of commercial interest stable in the time. Furthermore they do not need chemical process auxiliary agents as described in the prior art for the fine milling of crystalline imido-alkanperoxycarboxylic acids. Besides, they can be obtained also on an industrial scale with simplified processes and with reduced investment and working costs.

The imido-alkanperoxycarboxylic acids in the invention alpha crystalline form are stable in the time, even in case of prolonged storage, and subjected to the above described process they are spontaneously transformed into microcrystals of beta form, having the above average sizes and the desired characteristics for the preparation of compositions, as above described.

The following Examples illustrate with non limitative purposes the invention.

EXAMPLE 1A

PAP Preparation Having Alpha Crystalline Form by Mass-crystallization 100 ml of demineralized water "Micropure Grade" and 0.5 g of hydroxyethyliden-diphosphonic acid (HEDP) (Supplier Bozzetto: HEDP 10H60), are introduced in a 200 ml jacketed beaker equipped with an outlet valve on the bottom and the solution is heated up to about 78° C. Then 100 g of crystalline PAP of technical degree (Ausimont, Eureco® W type) are added. It is put under stirring at the rate of about 250 rpm and the PAP melting is expected, which takes place when the system temperature rises again to a value of about 78° C. At this temperature the two formed liquid phases, respectively the organic phase formed by the PAP eutectic with water and the aqueous phase, result transparent. The stirring is reduced to 20 rpm and the evident separation of the two phases with the heavier organic phase which gathers on the bottom is obtained.

About 250 ml of liquid nitrogen are drawn in a Dewar vessel, and a magnetic anchor is immersed therein to stir the liquid with a magnetic stirrer, positioning this vessel immediately under the outlet valve of the jacketed beaker containing on the bottom the melted organic phase.

The bottom valve of this is slowly opened and the melted liquid is let drip in the liquid nitrogen phase. The operation is interrupted as soon as the upper level of the melted organic phase in the jacketed beaker approaches the bottom valve. The solidified PAP is separated from the still liquid nitrogen, taking the solid with a round spatula, and transferring it into a small plastic tank resistant to low temperatures.

After having conditioned again the product at the room temperature, the PAP granules are dried by drying under vacuum, at about residual 10 mmHg, at a temperature not higher than 20° C. The specimen, weighing about 70 g of crystalline PAP is characterized by the X Ray Diffraction and Surface Infrared Spectroscopy (IR/S) techniques. The obtained spectra identify the alpha form.

X Rays: typical peaks at 17.5 and 19.0 and typical quadruplet at 24.2-25.0 [°2θ].

IR/S: typical peak with maximum absorption in the 1707-1712 $cm^{-1}$ zone (anhydrous crystals: absorption at 3450-3500 lower than 5%).

EXAMPLE 1B (COMPARATIVE)

PAP Preparation of Beta Crystalline Form (Crystalline Form of the Prior Art) by Mass-crystallization By initially operating according to the procedure of Example 1A, the melted organic phase formed by the PAP eutectic with water is fed to a beaker containing water at the temperature of about 40° C., and kept under stirring with a magnetic stirrer and a magnetic anchor. After the melt solidification, the solid separation from the liquid, the granular product is dried with the same method described to remove the residual water in Example 1A. Also this specimen is characterized by the X Ray Diffraction and the Surface Infrared Spectroscopy techniques. The obtained spectra identify the beta form.

X Rays: typical peaks at 18.0 and 18.7 and no typical quadruplet at 24.2-25.0 [°2θ].

IR/S: typical peak with maximum absorption in the 1699-1704 $cm^{-1}$ zone (anhydrous crystals: absorption at 3450-3500 lower than 5%).

EXAMPLE 1C (COMPARATIVE)

Example 1B has been repeated but by using water cooled at 15° C. The results are equal to those obtained in Example 1B.

EXAMPLE 2A

PAP Preparation of Beta Microcrystalline Form Starting from PAP of Alpha Crystalline Form In a beaker immersed in a thermostatic bath an aqueous dispersion of alpha crystalline PAP in demineralized water at 5% by weight of PAP is prepared, by adding to 473.5 ml of demineralized water at the temperature of 50° C., kept under stirring with an anchor and a magnetic stirrer, 500 ppm of antifoam DB 100 and 1,000 ppm of surfactant Hostapur® SAS and 26.50 g of crystalline PAP in alpha form, of technical degree (titre: 94.3%) having average sizes higher than 100 micron. After 10 minutes of stirring at 50° C., the beaker is removed from the thermostatic bath and the aqueous suspension is transferred in a graduated cylinder. It is let rest at room temperature in the graduated cylinder. In the suspension no thickenining of solid phase on the cylinder bottom is observed, both after two hours and after 48 hours, and a separation of supernatant clear liquid phase of no more than 20% by volume even after 10 days is noticed.

One sample of said aqueous dispersion, observed with optical microscope (50 and 500 magnifications) shows that the PAP crystals dispersed in the water have average sizes lower than 10 micron, in particular lower than 2 micron. These microcrystals, recovered and studied by means of the analytical techniques of Example 1, show the same characteristics of beta form crystals and no longer those of the starting alpha form crystals.

EXAMPLE 2B (COMPARATIVE)

Repetition of Example 2A but by Starting from Crystalline PAP in Beta Form.

An aqueous dispersion of crystalline PAP in demineralized water at 5% by weight of PAP is prepared, as described in Example 2A, by adding to 471.9 ml of demineralized water 500 ppm of antifoam DB 100 and 1000 ppm of surfactant Hostapur® SAS and 28.1 g of crystalline PAP in beta form of technical degree (titre: 89%), having average sizes higher than 100 micron, in particular 80% of the particles being comprised between 100 and 200 micron. After 10 minutes of stirring at 50° C., the beaker is removed and the suspension is transferred into a graduated cylinder, as in Example 2A. Already after 10 minutes rest at room temperature in the graduated cylinder, it is observed the clear separation of a supernatant aqueous phase for 60% of the total volume and the sedimentation of a precipitate on the bottom. The separation of the supernatant aqueous phase increases after 2 hours to more than 70% of the total volume.

A solid specimen, examined by optical microscope and by the techniques mentioned in Example 1A, shows that the crystals have unchanged sizes and properties with respect to those of the starting PAP crystals in beta form.

EXAMPLE 3

Dissolution Rate of PAP Crystals of Beta Form, and of PAP Microcrystals of Beta Form Obtained from PAP Crystals of Alpha Form According to Example 2A A test is carried out for the determination of the dissolution time, by dispersing 100 mg of anhydrous crystalline PAP (base 100%), respectively of crystals and microcrystals (sizes lower than 10 micron) of PAP in beta form, obtained as from Examples 2B and 2A respectively, in one litre of solution prepared with water having a 10° F. hardness and 1.70 g of standard detergent base, free from bleach aditives (detergent IEC type B, with phosphates—Publication IEC 60,456), kept under stirring and thermostated at the temperature of 40° C.

Successive samples of liquid phase, carefully filtered on filter of 0.45 micron, are drawn and the PAP concentration in solution is determined by HPLC.

The necessary times for the dissolution of 90% of the crystalline PAP initially dispersed in the aqueous solution are of 30 and 15 minutes respectively for the used crystals and microcrystals of PAP in beta form.

Said times are determined by drawing some curves reporting in ordinate the PAP concentration dissolved in the aqueous phase (determined by HPLC) and in abscissae the sample drawing time, taking as 100% the PAP concentration asymptotically obtained at infinite time.

The previous test is repeated by dispersing 70 mg of anhydrous crystalline PAP (base 100%), respectively of crystals and microcrystals (sizes lower than 10 micron) of PAP in beta form, obtained as from Examples 2B and 2A respectively, in one litre of aqueous solution, prepared as above, stirred and thermostated at the temperature of 25° C.

Successive samples of liquid phase, carefully filtered on filter of 0.45 micron, are drawn, and the PAP concentration in solution is determined by HPLC.

The necessary times for the dissolution of 90% of the crystalline PAP initially dispersed in the aqueous solution are of 60 and 14 minutes respectively for the used crystals and microcrystals of PAP in beta form.

EXAMPLE 4A (COMPARATIVE)

Preparation of a Typical PAP Composition Having an Aqueous Basis and Evaluation of the Respective Bleach Activity A typical composition having an aqueous basis at 10% by weight of active PAP is prepared with crystalline PAP in beta form, milling it by a colloid mill and subsequently by a high flow rate mill with impact and cavitation and adding then, under stirring for 30 minutes at the temperature of 45° C., the following substances in the indicated amounts, expressed in percentages by weight on the final composition:
  non-ionic surfactant 2.5%,
  xanthan rubber 0.50%,
  HEDP 0.1%.

The obtained dispersion is chemically and physically stable even after exposure at the temperature of 35° C. in a stove for 7 days. The initial viscosity of 670 mpa.s becomes 730 mpa.s after 7 days at 35° C.

The bleach activity of said composition is evaulated according to a laboratory test, by treatments in combination with HD detergent (Heavy Duty) at 40° C. for 30 minutes, or in combination with LD detergent at 30° C. (Light Duty) for 30 minutes, of a set of test cotton tissues dirtied with the following types of artificial dirt EMPA: art. 114 (red wine), art. 167 (tea) and art. 164 (grass), obtaining a white degree of 70, 67.5 and 63 (HD detergent), or of 72, 73 and 64.5 (LD detergent) respectively.

EXAMPLE 4B

Repetition of Example 4A Using Crystalline PAP in Alpha Form

The same standard composition having an aqueous basis at 10% by weight of active PAP is prepared with crystalline PAP in alpha form. Crystals are milled for 5 minutes with Brown® Minipimer mill and, by maintaining under stirring for 30 minutes at the temperature of 45° C., the following substances are added in the indicated amounts, expressed in percentages by weight on the final composition:
  non ionic surfactant 2.5%,
  xanthan rubber 0.10%,
  HEDP 0.10%.

The obtained dispersion is chemically and physically stable, even after exposure at the temperature of 35° C. in a stove for 7 days. The initial viscosity of 570 mPa.s becomes 580 mPa.s after 7 days at 35° C.

The bleach activity of this formulation is evaluated by using the same above mentioned laboratory test, by treatments in combination with HD detergent at 40° C. for 30 minutes, or in combination with LD detergent at 30° C. for 30 minutes, of a set of test cotton tissues dirtied with the following types of artificial dirt EMPA: art. 114 (red wine), art. 167 (tea) and art. 164 (grass), obtaining a bleach degree of 71, 69.5 and 63 (HD detergent), or 73, 73.5 and 65.5 (LD detergent) respectively.

EXAMPLE 5

Dissolution Rate of the Crystalline PAP in Beta Form Present in Liquid Compositions Having an Aqueous Basis Three compositions having an aqueous basis of commercial interest called respectively A, B, C, containing in suspension PAP crystals in beta form are prepared and the PAP dissolution times thereof are determined by the methods described in Example 3, by dispersing a sample of the single composition to be tested in 1 litre of solution, prepared with water having a 10° F. hardness, and 1.70 g of standard detergent base of Example 3, at the temperature of 25° C.

The three compositions A, B and C subjected to the test are respectively obtained as follows:
  Formulation A:
    60 g of PAP of alpha form of technical degree,
    1.50 g of xanthan rubber,
    10 g of non ionic surfactant,
    0.6 g of antifoam DB100
    are dispersed in 928 g of water at 50° C. and treated for 5 minutes by Silverson equipment, then with blade mechanical stirrer for 30 minutes at 50° C. and subsequently for 30 minutes at room temperature.
    The obtained composition A has a titre in active PAP of 5.02% and a viscosity at 25° C. of 120 mPa.s. The PAP crystals dispersed in the aqueous phase have sizes lower than 10 micron.

Formulation B:
  60 g of PAP of alpha form of technical degree,
  1.0 g of xanthan rubber,
  3.4 g of anionic surfactant Hostapur®SAS,
  0.6 g of antifoam DB100
are dispersed in 935 g of water at 50° C. and treated for 5 minutes with Silverson equipment, then with blade mechanical stirrer for 30 minutes at 50° C. and subsequently for 30 minutes at room temperature.

The obtained composition B has a titre in active PAP of 5.0% and a viscosity at 25° C. of 300 mPa.s. The PAP crystals dispersed in the aqueous phase have sizes lower than 2 micron.

The composition C is the same comparative composition described in Example 4A.

With the test to determine the dissolution times at 25° C. of the crystalline PAP contained in the three compositions A, B and C, the values reported in Table 2 are obtained, wherein $T_{98.0}$, $T_{99.0}$ and $T_{99.8}$ show the necessary times for the dissolution respectively of 98.0%, 99.0% and 99.8% of the PAP initially introduced in the test solution.

Said times and respective percentages are determined as described in Example 3.

From the Table it results that the time necessary for the PAP dissolution of the compositions A and B is undoubtedly lower than the time requested by the composition C of the prior art.

TABLE 1

Examples 4A comp. and 4B: comparison between the results (white degree) obtained in the washing tests using mixtures containing HD detergent, or respectively LD, and compositions formed by (% by weight): 2.5% of non ionic surfactant, 0.10% HEDP, and respectively the % of xanthan rubber and 10% of PAP of the type as indicated in the Table

| | Ex. 4A Comp | Ex. 4B |
|---|---|---|
| PAP and xanthan rubber in the composition | | |
| PAP | beta | alpha |
| xanthan rubber (% by weight) | 0.5 | 0.1 |
| Washing tests Composition + HD surfactant White degree: | | |
| art. 114 (red wine) | 70 | 71 |
| art. 167 (tea) | 67.5 | 69.5 |
| art. 164 (grass) | 63 | 63 |
| Washing tests Composition + LD surfactant White degree: | | |
| art. 114 (red wine) | 72 | 73 |
| art. 167 (tea) | 73 | 73.5 |
| art. 164 (grass) | 64.5 | 65.5 |

TABLE 2

Example 5, dissolution rate of the crystalline PAP present in the liquid compositions having an aqueous basis A, B and C.

| Compositions | $T_{98.0}$ min | $T_{99.0}$ min | $T_{99.8}$ min |
|---|---|---|---|
| A | <5 | 7 | 20 |
| B | <<5 | <5 | 10 |
| C | 5 | 15 | 65 |

$T_{98.0}$, $T_{99.0}$ and $T_{99.8}$ show the times necessary for the dissolution respectively of 98.0%, 99.0% and 99.8% of the PAP initially introduced in the test solution.

The invention claimed is:

1. An imido-alkanpercarboxylic acid represented by formula (I):

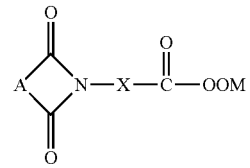

formula (I)

wherein A is

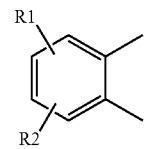

wherein:
R1 is hydrogen, chlorine, bromine, $C_1$-$C_{20}$ alkyl, $C_2$-$C_{20}$ alkenyl, aryl, or alkylaryl, R2 is hydrogen, chlorine, bromine —$SO_3M$, —$CO_2M$, —$CO_3M$ or —$OSO_3M$, M is hydrogen, an ammonium alkaline metal, or an alkaline-earth metal equivalent, and X is a $C_1$-$C_{19}$ alkylene or an arylene;

wherein said imido-alkanpercarboxylic acid is in a crystalline form of alpha that is stable at storage at the solid state, but when dispersed in water is capable of being transformed into one or more crystals of beta crystalline form that are stable in aqueous environment, wherein said one or more crystals of beta crystalline form have an average size of lower than 30 microns, and wherein the respective spectra of the alpha crystalline form obtained by X-ray Diffraction and Surface Infrared Spectroscopy techniques show, with respect to the spectra of the beta form of the same peracid, exhibit a different spectral X-ray image and a typical absorption shift in the 1697-1707 $cm^{-1}$ zone by Surface Infrared Spectroscopy towards higher frequencies, of the order of 10 $cm^{-1}$.

2. The imido-alkanpercarboxylic acid according to claim 1, wherein the acid is ε-phthalimido-peroxyhexanoic acid in alpha crystalline form, and has the following chemico-physical parameters:

X-ray spectrum showing peaks at $2\theta=17.5°$ and $19.0°$ and quadruplet at $2\theta=24.2°$-$25.0°$, and Surface Infrared Spectroscopy spectrum showing a peak with maximum absorption in the 1707-1712 $cm^{-1}$ zone, for an anhydrous crystal, having a water absorption at 3450-3500 $cm^{-1}$ lower than 5%.

3. A process for the preparation of said imido-alkanperoxycarboxylic acid of claim 1, said process comprising:

I) peroxidating, in the presence of hydrogen peroxide and of a strong acid at a temperature of between 5° C.-50° C., an imido-alkancarboxylic acid precursor obtained by reacting:

a) an anhydride represented by formula (II):

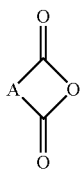

formula (II)

or the corresponding acid,
with
b1) an aminoacid represented by formula (III):

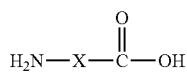

formula (III)

or
b2) a lactam represented by formula (IV):

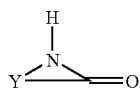

formula (IV)

Y having the meanings of X; and
c) water;
at temperatures in the range 1000° C.-2500° C., under pressure of an inert gas from 1 to 30 bar, for a reaction time of from 2 to 20 hours;
II) obtaining of a melted phase of eutectic composition of said imido-alkanperoxycarboxylic acid of formula (I) by heating a suspension in water of said imido-alkanperoxycarboxylic acid until the complete melting of the solid, said eutectic having a composition on a molar basis of no more than two moles of water/imido-alkanpercarboxylic acid;
III) separating said melted organic phase of eutectic composition from the aqueous phase in balance and recovering a melted organic phase comprising said imido-alkanpercarboxylic acid;
IV) quenching said melted organic phase to obtain said crystalline form of alpha, stable at the solid state.

4. The process according to claim 3, wherein said quenching is carried out by dripping said melted organic phase of eutectic composition in liquid nitrogen.

5. The process according to claim 3, wherein said quenching is carried out by dripping said melted organic phase of eutectic composition in cold water, under stirring, having a temperature lower than 15° C.

6. The process according to claim 3, wherein said quenching is carried out by percolating said melted organic phase on a metal surface, or on two metal surfaces, coupled and cooled at temperatures lower than 30° C.

7. The process according to claim 3, wherein in step I) the ratio by moles between a/(b1 or b2)/c is in the range 1/0.8-:1.2/0.5:3.

8. The process according to claim 3, wherein in step I) the anhydride a) or said corresponding acid is reacted with said lactam b2).

9. The process according to claim 3, wherein said anhydride or said corresponding acid is selected from the group consisting of: succinic, glutaric, maleic, trimellitic, phthalic, pyromellitic, alkyl-succinic, and alkenyl-succinic anhydride.

10. The process according to claim 3, wherein said amino acid is selected from the group consisting of: omega-aminobutyric, omega-aminovalerianic, omega-aminocaproic and omega-aminolauric acid.

11. The process according to claim 3, wherein said lactam is selected from the group consisting of: gamma-pyrrolidone, delta-piperidone, epsilon-caprolactam, and omega-laurolactam.

12. The process according to claim 3, wherein in step I) the temperature is in the range 130° C.-180° C. and the pressure is in the range 4-8 bar.

13. The process according to claim 3, wherein said imido-alkanpercarboxylic acid is selected from the group consisting of phthalimido-peracetic acid, ε-phthalimido peroxyhexanoic acid, 3-phthalimido-perpropionic acid, 4-phthalimido-perbutyric acid, 2-phthalimido-diperglutaric acid, 2-phthalimido-dipersuccinic acid, 3-phthalimido-perbutyric acid, 2-phthalimido-perpropionic acid, 3-phthalimido-diperadipic acid, naphthalimido-peracetic acid, 2-phthalimido-monopersuccinic acid.

14. The process according to claim 3, wherein in step II) one or more sequestrants are added in the aqueous phase.

15. A process, comprising dispersing the imido-alkanpercarboxylic acid according to claim 1 in water.

16. A process, comprising dispersing the imido-alkanpercarboxylic acid according to claim 2 in water.

* * * * *

UNITED STATES PATENT AND TRADEMARK OFFICE
CERTIFICATE OF CORRECTION

PATENT NO. : 7,468,387 B2  
APPLICATION NO. : 10/519835  
DATED : December 23, 2008  
INVENTOR(S) : Ugo Piero Bianchi et al.

It is certified that error appears in the above-identified patent and that said Letters Patent is hereby corrected as shown below:

Column 14, line 32, "X is a $C_1$-$C_{19}$ alkylene or an arylene;"
   should read -- X is $C_1$-$C_{19}$ alkylene or an arylene; --;
   line 59, "for an anhydrous crystal, having a water absorption at"
   should read -- for anhydrous crystal, having a water absorption at --.

Signed and Sealed this

Twenty-fourth Day of November, 2009

David J. Kappos  
*Director of the United States Patent and Trademark Office*